United States Patent [19]
Rogers et al.

[11] Patent Number: 6,120,515
[45] Date of Patent: *Sep. 19, 2000

[54] COMPOSITE ATHERECTOMY CUTTER

[75] Inventors: Larry Rogers, Half Moon Bay; John Thomas Buckley, San Jose; Ron Ray Hundertmark, San Mateo; Ferolyn T. Powell, San Carlos; Charles Milo, Union City; Anthony J. Castro, San Francisco, all of Calif.

[73] Assignee: Devices for Vascular Intervention, Inc., Redwood City, Calif.

[ * ] Notice: This patent is subject to a terminal disclaimer.

[21] Appl. No.: 08/895,106

[22] Filed: Jul. 16, 1997

Related U.S. Application Data

[62] Division of application No. 08/597,603, Feb. 6, 1996, Pat. No. 5,733,296.

[51] Int. Cl.[7] ............................ A61M 29/00; A61B 17/00
[52] U.S. Cl. ...................... 606/159; 606/170; 128/662.06
[58] Field of Search ................................ 606/1, 159, 170, 606/171, 180; 604/22; 128/660.03, 662.06

[56] References Cited

U.S. PATENT DOCUMENTS

| | | |
|---|---|---|
| Re. 33,569 | 4/1991 | Gifford, III et al. . |
| 4,669,469 | 6/1987 | Gifford, III et al. . |
| 4,771,774 | 9/1988 | Simpson et al. . |
| 4,781,186 | 11/1988 | Simpson et al. . |
| 4,794,931 | 1/1989 | Yock . |
| 4,883,458 | 11/1989 | Shiber . |
| 4,886,490 | 12/1989 | Shiber . |
| 4,979,939 | 12/1990 | Shiber . |
| 4,979,951 | 12/1990 | Simpson . |
| 5,000,185 | 3/1991 | Yock . |
| 5,007,917 | 4/1991 | Evans . |
| 5,024,234 | 6/1991 | Leary et al. . |
| 5,071,425 | 12/1991 | Gifford, III et al. . |
| 5,078,717 | 1/1992 | Parins et al. . |
| 5,084,010 | 1/1992 | Plaia et al. . |
| 5,085,662 | 2/1992 | Willard . |
| 5,087,265 | 2/1992 | Summers . |
| 5,092,873 | 3/1992 | Simpson et al. . |
| 5,108,411 | 4/1992 | McKenzie . |
| 5,135,531 | 8/1992 | Shiber . |
| 5,156,510 | 10/1992 | Reger . |
| 5,158,564 | 10/1992 | Schnepp-Pesch et al. . |
| 5,226,847 | 7/1993 | Thomas, III et al. . |
| 5,226,909 | 7/1993 | Evans et al. . |
| 5,250,059 | 10/1993 | Andreas et al. . |
| 5,314,438 | 5/1994 | Shturman . |
| 5,427,107 | 6/1995 | Milo et al. . |
| 5,429,136 | 7/1995 | Milo et al. . |
| 5,507,760 | 4/1996 | Wynne et al. . |
| 5,569,276 | 10/1996 | Jang et al. . |

*Primary Examiner*—Michael Buiz
*Assistant Examiner*—William Lewis
*Attorney, Agent, or Firm*—Peninsula IP Group; Douglas A Chaikin

[57] ABSTRACT

An athetectomy catheter is disclosed having a composite cutter which is capable of cutting material, including hardened plaque, from a biological conduit. The composite cutter has a cutter and a sensor mount. The cutter has a proximal end and a distal end with a cutting edge. The proximal end of the cutter bonds with the sensor mount. The sensor mount is adaptable for holding a sensor and attaching to a cutter torque cable of an atherectomy catheter. Typically, the atherectomy catheter has a cutter housing with a window. The composite cutter is positioned in the cutter housing and moves in response to movement of the cutter torque cable to cut material from the biological conduit via the window.

9 Claims, 7 Drawing Sheets

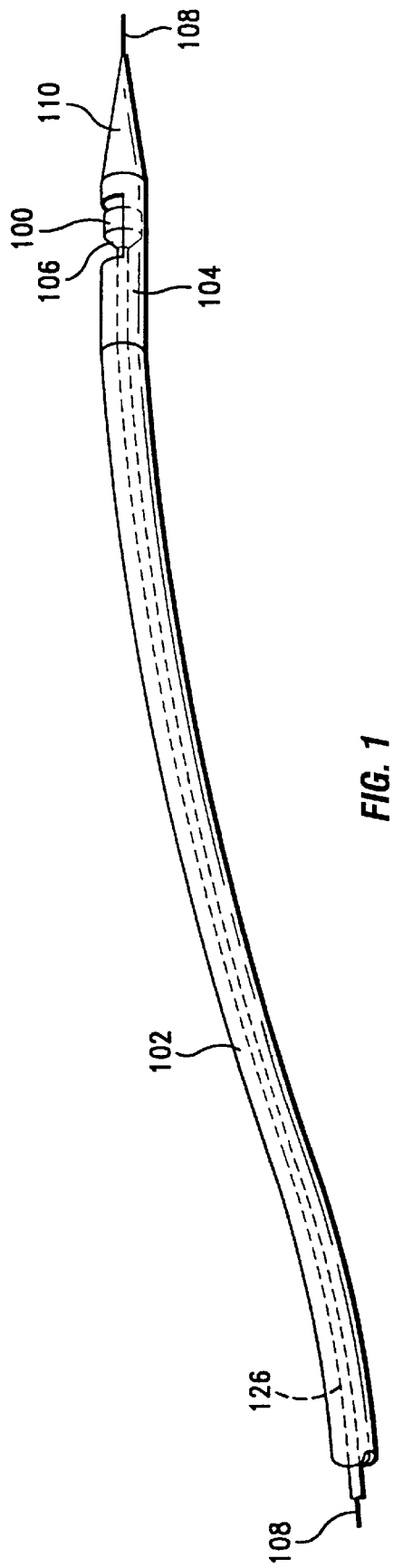
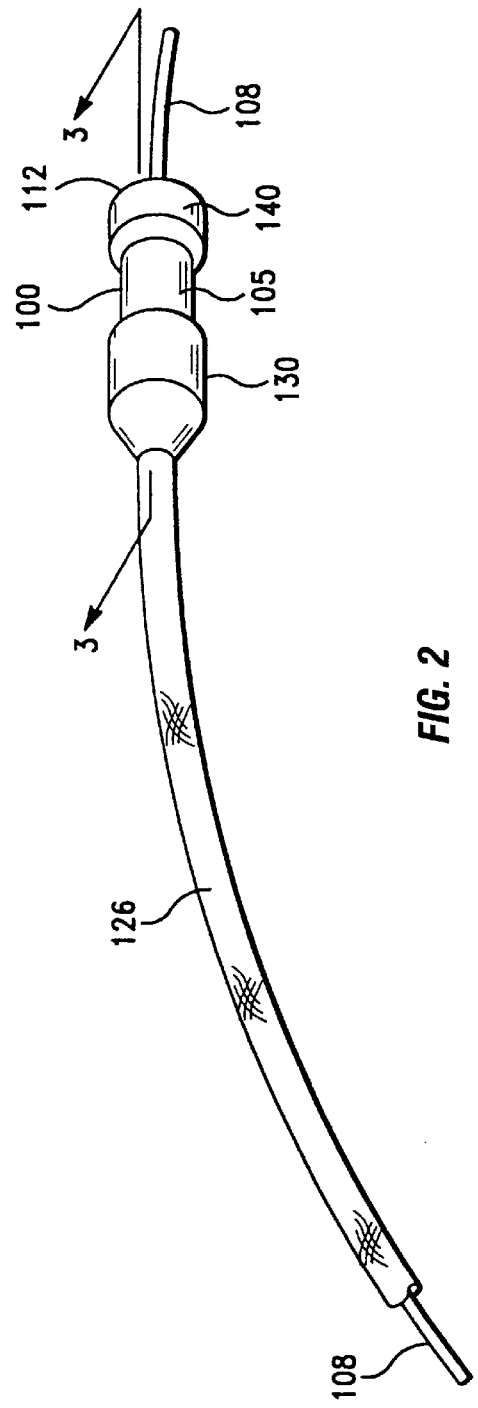
FIG. 1
FIG. 2

COMPOSITE ATHERECTOMY CUTTER

This is a divisional of application Ser. No. 08/597,603 filed on Feb. 6, 1996, now U.S. Pat. No. 5,733,296.

BACKGROUND OF THE INVENTION

1. Field of the Invention

This invention relates to atherectomy catheters, and more specifically to atherectomy catheters having a composite tissue cutter formed with a cutter and a sensor mount.

2. Previous Art

Atherosclerosis is a condition characterized by the deposit of fatty deposits (atheromas) which adhere to the internal lining of human blood vessels. Atherosclerosis manifests itself in a variety of ways. Angina, hypertension, myocardial infarction, and strokes may result from untreated atherosclerosis.

Regions of a blood vessel blocked by atheroma, plaque, or other material are called stenotic regions. The blocking material is known as stenotic material or plaque. Stenotic material is often relatively soft and tractable. However, stenotic material can also be calcified and hard. Plaque may be harder than ordinary tissue and may firmly adhere to the walls of blood vessels and other biological conduits.

Atherectomy catheters are used to remove stenotic material from the inside of blood vessels. A typical atherectomy catheter has a distal end which inserts into a biological conduit to remove plaque. A housing with a nose cone attaches to the distal end. A cutter is enclosed in the housing. A cutter torque cable extends within the catheter and attaches to the cutter. The cutter cuts stenotic material from the inside of a blood vessel in response to movement of the cutter torque cable when the catheter is appropriately positioned.

During an atherectomy procedure, an atherectomy catheter is inserted into the femoral artery of a patient by a physician. The physician manipulates the catheter and positions the housing of the catheter adjacent a stenotic region having stenotic material within the blood vessel. The cutter is manipulated for the removal of stenotic material. The removed stenotic material is captured by the nosecone of the catheter.

Atherectomy catheters having tissue cutters have enjoyed substantial success and acceptance in the medical community. Atherectomy catheters have been most effective when used for the removal of relatively soft (e.g. non-calcified) stenotic material. The removal of hard material such as calcified plaque, however, has been more problematic. When the cutter of an atherectomy catheter encounters calcified plaque, for example, the cutting edge of the cutter becomes dull. Hardened plaque is difficult to remove with a dull cutter.

Cutters fabricated from harder materials have been developed to minimize dulling. The harder materials enable cutters to cut hardened calcified plaque without dulling or deforming. Examples of such cutters are disclosed in U.S. Pat. No. 5,507,760, Issue Date, Apr. 16, 1996 to Wynne et al., entitled "Cutter Device", the disclosure of which is incorporated herein by reference.

The state of the art has advanced. The use of cutters having ultrasonic imaging sensors is now known. An example of a cutter having an ultrasonic imaging transducer is described in U.S. Pat. No. 5,000,185, issued Mar. 3, 1991 to Yock. Ultrasonic imaging sensors perform various useful functions such as safely guiding an atherectomy device through a vascular system, for example. Ultrasonic imaging sensors inspect the stenotic material to be cut and have proven to be useful when employed with devices such as atherectomy catheters.

Proper attachment of a sensor to the cutter of an atherectomy device should align the sensor with respect to the cutter and protect the sensor from damage. Attachment of the sensor is effectively accomplished by machining a portion of the cutter and attaching the sensor to the machined portion of the cutter. In this way, a firm base for attachment of the sensor is established. Machining is difficult, however, for a variety of reasons. The hardness of the atherectomy cutters in combination with the very small size of atherectomy cutters makes machining of the cutters difficult. Adapting a hard cutter to house a sensor is expensive and impractical when accomplished by common machining methods.

It is desirable to provide a device having a cutter which is capable of cutting calcified deposits without dulling. It is also desirable to provide a device which is adapted to hold a sensor which can guide the device through the vasculature of a patient.

SUMMARY OF THE INVENTION

The following objects of the invention are presented to describe the present invention by way of example only and should not be read in any way which limits the scope of the appended claims.

It is an object of this invention to provide a device having a cutter which is hard enough to cut calcified tissue.

It is an object of this invention to provide a device which is capable of aligning a cutter with a sensor to improve atherectomy procedures.

It is an object of this invention to provide a device which has a machinable portion to house a sensor and a hardened portion for cutting hardened tissue.

In accordance with the above objects and those that will be mentioned and will become apparent below, the present invention is an atherectomy device for cutting material from the inside of a biological conduit, comprising:

a catheter having a housing and a rotatable cutter torque cable, the catheter being insertable into the biological conduit, the cutter torque cable extending through the catheter to the housing;

a sensor mount having a proximal end and a distal end, the proximal end of the sensor mount being attached to the cutter torque cable and being adaptable for holding a sensor, the distal end of the sensor mount including a tapered portion, the sensor mount rotates with the cutter torque cable; and a cutter having a proximal end, a distal end, a faded portion, and a cutting edge, the cutting edge being formed on the distal end of the cutter, the tapered portion of the sensor mount being bonded to the faded portion of the cutter, the cutter being attached to the sensor mount to rotate with the cutter torque cable, whereby when the catheter is inserted into a biological conduit, the cutter and the sensor mount move within the housing in response to movement of the cutter torque cable to cut material from inside of the biological conduit.

In a preferred embodiment, the distal end of the sensor mount includes a tapered portion, the cutter includes a faded portion. The tapered portion of the sensor mount bonds with the faded portion of the cutter. The tapered portion of the sensor mount has external splines and an annular recess. The faded portion of the cutter has internal splines. The proximal end of the cutter has an annular lock. The annular lock and the internal splines of the cutter mechanically interlock with the annular recess and the external splines of the sensor mount respectively.

In a preferred embodiment, the proximal end of the sensor mount defines an interior which is connectable to the cutter torque cable. The proximal end of the sensor mount includes an attachment hole which enables the sensor mount to be connectable with the cutter torque cable.

In a preferred embodiment, the sensor mount is fabricated from machinable grade stainless steel and the cutter is fabricated from tungsten carbide. The cutter includes a coating to increase the hardness of the cutting edge. In a variation of this preferred embodiment, the coating is fabricated from titanium nitride.

In a preferred embodiment the cutter defines an interior having an internal ridge. The sensor mount inserts through the distal end of the cutter. The proximal end of the sensor mount contacts the interior of the cutter at the proximal end of the cutter. The distal end of the sensor mount contacts the internal ridge. Accordingly, the interior, the proximal end and the internal ridge of the cutter cooperate to hold the sensor mount and the cutter together.

In a preferred embodiment, the sensor mount includes a trough. The trough being configured having a geometry adaptable for holding a sensor. In a variation of this embodiment, the sensor mount includes an interior, the trough extends into the interior of the sensor mount. In a variation of this embodiment, the sensor mount includes a periphery. The periphery being adaptable for bonding to a sensor.

In a preferred embodiment, the cutter includes an interior and an internal seat formed with the interior. The sensor mount includes an exterior and a cap. The cap of the sensor mount contacts the proximal end of the cutter. The exterior of the sensor mount bonds to the interior of the cutter and the distal end of the sensor mount contacts the internal seat of the cutter.

In a preferred embodiment, the cutter includes an annular face, a cylindrical extension, and an externally defined annular ring. The sensor mount includes an internal annular groove. The cylindrical extension extends perpendicularly from the annular face of the cutter, the annular ring encircles a portion of the cylindrical extension, the annular ring snaps into the internal annular groove in the sensor mount to mechanically interconnect the sensor mount and the cutter.

It is an advantage of this invention to provide a cutter which includes a cutting surface hard enough to cut calcified tissue.

It is an advantage of this invention to provide a cutter which is capable of housing an imaging sensor to improve atherectomy procedures.

It is an advantage of this invention to provide a cutter which is machinable to appropriately house an sensor to improve atherectomy procedures.

BRIEF DESCRIPTION OF THE DRAWINGS

For a further understanding of the objects and advantages of the present invention, reference is made to the following detailed description, in conjunction with the accompanying drawing, in which like parts are given like reference numerals and wherein:

FIG. 1 is a perspective view of an atherectomy catheter and a composite cutter in accordance with the present invention.

FIG. 2 is a perspective view of a cutter torque cable and the composite cutter of FIG. 1 in accordance with the present invention.

DETAILED DESCRIPTION OF THE INVENTION

Figure 3:
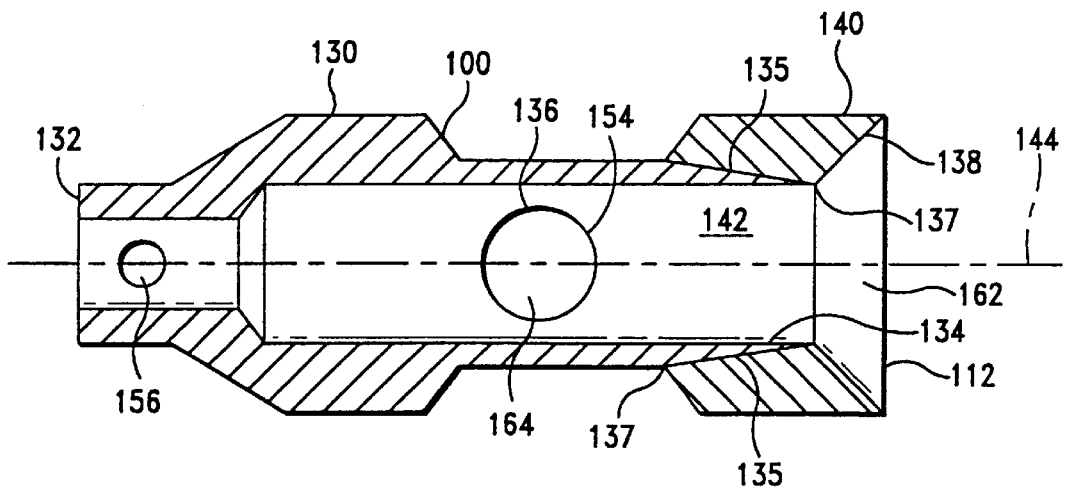
FIG. 3 is a cross-sectional view of an embodiment of the composite cutter of FIG. 2 as seen along the line 3—3.

With particular reference to FIG. 1, an atherectomy catheter 102 having a cutter housing 104, a window 106, a composite cutter 100, a nose cone 110, a cutter torque cable 126 and a guide wire 108 is shown. The cutter housing 104 encloses the composite cutter 100. The window 106 of the cutter housing 104 aligns with the composite cutter 100. The nose cone 110 attaches to the cutter housing 104. The guide wire 108 extends through the atherectomy catheter and beyond the nosecone 110.

During an atherectomy, for example, the atherectomy catheter 102 is inserted into the vascular system of a patient. The window 106 invaginates material from the interior wall of a blood vessel. The composite cutter 100 reciprocates within the housing and severs the invaginated material. The severed material is stored in the nosecone 110. An example of an operable atherectomy catheter and the use thereof is disclosed by Gifford III et al. in U.S. Pat. No. 5,471,125, entitled "Atherectomy Catheter and Method of Forming the Same", the disclosure of which is incorporated herein by reference. The operation of a sensor with an atherectomy cutter is disclosed in U.S. Pat. No. 5,427,107, issued Jun. 27, 1995 to Milo et al., entitled "Optical Encoder for Catheter Device", which is commonly assigned and incorporated herein by reference.

With particular reference to FIG. 2, there is shown the cutter torque cable 126, the composite cutter 100 and the guide wire 108. The guide wire 108 extends axially through the composite cutter 100 and the cutter torque cable 126. The composite cutter 100 includes a sensor mount 130 and a cutter 140. The cutter 140 has a cutting edge 112. The composite cutter 100 aligns coaxially with and attaches to the cutter torque cable 126.

The cutting edge 112 has an arcuate shape. The cutting edge 112 is sharp, being between 5–10 microns thick. The cutting edge 112 has a hardness relatively greater than the hardness of the sensor mount 130. A cutting edge 112 having a Rockwell "A" hardness of 90, or harder is preferred because such an edge is hard enough to cut calcified plaque from a biological conduit. In an embodiment of the present invention, the sensor mount 130 is fabricated from a machinable grade of stainless steel and the cutting edge 112 is fabricated from tungsten carbide.

The cutting edge 112 can be of various shapes and configurations. For example, the cutting edge 112 can be configured having cutting surfaces of types described in co-pending U.S. Pat. No. 5,507,760, Issue Date, Apr. 16, 1996 to Wynne et al., entitled "Cutter Device".

The composite cutter 100 is generally cylindrical in shape. The composite cutter 100 includes a middle portion 105 which is relatively narrower than the remainder of the composite cutter 100.

When the atherectomy catheter 102 (see FIG. 1) inserts into a biological conduit (e.g. a blood vessel) and window 106 aligns adjacent to stenotic material. An operator manipulates the cutter torque cable 126 to reciprocate the composite cutter 100. A motor drive unit (not shown) rotates the cutter torque cable 126. The composite cutter 100 and cutter torque cable 126 are designed to rotate within the range of 1500–2500 revolutions per minute (RPM). When the cutter torque cable 126 rotates and advances, the composite cutter 100 rotates and advances to cut tissue which extends into the cutter housing 104 via the window 106. An example of a cutter torque cable 126 is described in copending U.S. patent application Ser. No. 08/606,678, filed Feb. 26,1996 entitled "Flexible Composite Drive Shaft for Transmitting Torque" by Milo, et al., Attorney Docket No. DEVI1434CON, which is a file wrapper continuation of U.S. patent application Ser. No. 08/165,058, filed Dec. 9, 1993, entitled "Composite Drive Shaft" by Milo, et al.

With particular reference to FIG. 3, there is shown an embodiment of the composite cutter 100 of FIG. 2. The sensor mount 130 has a proximal end 132, a distal end 134, an interior 142 and a tapered portion 135. The cutter 140 has a proximal end 139, a distal end 138 having a cutting edge 112, an interior surface 162, and a faded portion 137.

The proximal end 132 of the sensor mount 130 is attachable to a cutter torque cable (see FIG. 2). The tapered portion 135 of the sensor mount 130 connects with the faded portion 137 of the cutter 140. Tapered, for the purposes of the present invention, means a male connector having an end with a narrow diameter which slopes to a relatively wider diameter, the tapered slope being constant. Faded, for the purposes of the present invention means a female connector having an open mouth with an end having a wide diameter which slopes to a relatively narrower inner diameter, the faded slope being constant.

The tapered portion 135 of the sensor mount 130 mechanically interlocks (i.e. forms a mechanical force-fit) with the faded portion 137 of the cutter 140. The cutter 140 and the sensor mount 130 interconnect in coaxial alignment. The interconnection between the sensor mount 130 and cutter 140 is reinforced by any of a number of interconnection techniques (processes) such as brazing, welding, soldering or adhesive bonding. The interconnection between the sensor mount 130 and the cutter 140 protects, aligns and holds the sensor 164 relative to the cutter 140 during operation of the composite cutter.

Figure 4:
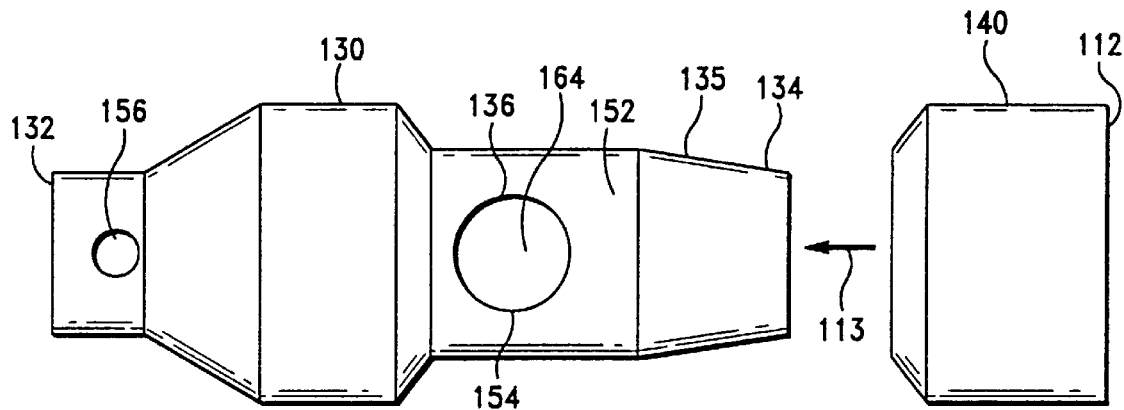
FIG. 4 is an exploded view of a variation of the embodiment of the composite cutter of FIG. 3.

With particular reference to FIG. 4, there is shown an exploded side view of the composite cutter 100 depicted in FIG. 3. The sensor mount 130 and the cutter 140 join together in the direction of the arrow 113. The proximal end 132 of the sensor mount 130 has an attachment hole 156. The attachment hole 156 facilitates the selected process which interconnects the sensor mount 130 and the cutter torque cable 126 e.g. soldering, brazing, or welding. The sensor 164 is positioned within the interior 142 of the sensor mount 130. The sensor 164 attaches to the interior 142 by adhesive bonding for example. An opening 154 is defined on the surface 152 of the middle portion 105 of the composite cutter 100. The opening 154 is circular in shape. The sensor 164 is circular in shape and fits within the opening 154. The opening 154 is defined on the sensor mount 130 and permits sensory communication between the sensor 164 and the environment which surrounds the composite cutter 100.

Figure 5:
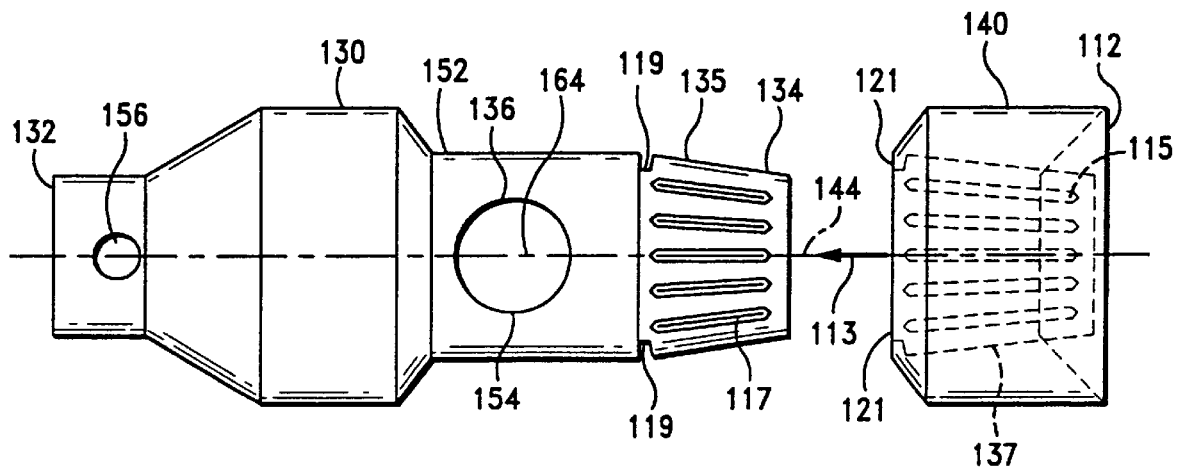
FIG. 5 is an exploded view of a variation of the embodiment of the composite cutter of FIG. 3.

With particular reference to FIG. 5, a variation of the embodiment of the composite cutter 100 illustrated in FIG. 4 is shown. The tapered portion 135 of the sensor mount 130 is formed with at least one external spline 117. The faded portion 137 of the cutter 140 is formed with at least one internal spline 115. The internal spline 115 and the external spline 117 mechanically interlock.

When internal spline 115 and the external spline 117 mechanically interlock, the cutter 140 and the sensor mount 130 align coaxially. The sensor mount 130 includes an annular recess 119 which circumscribes the external spline 117. The proximal end 139 of the cutter 140 includes an annular lock 121. The annular lock 121 snaps into the annular recess 119.

Figure 6:
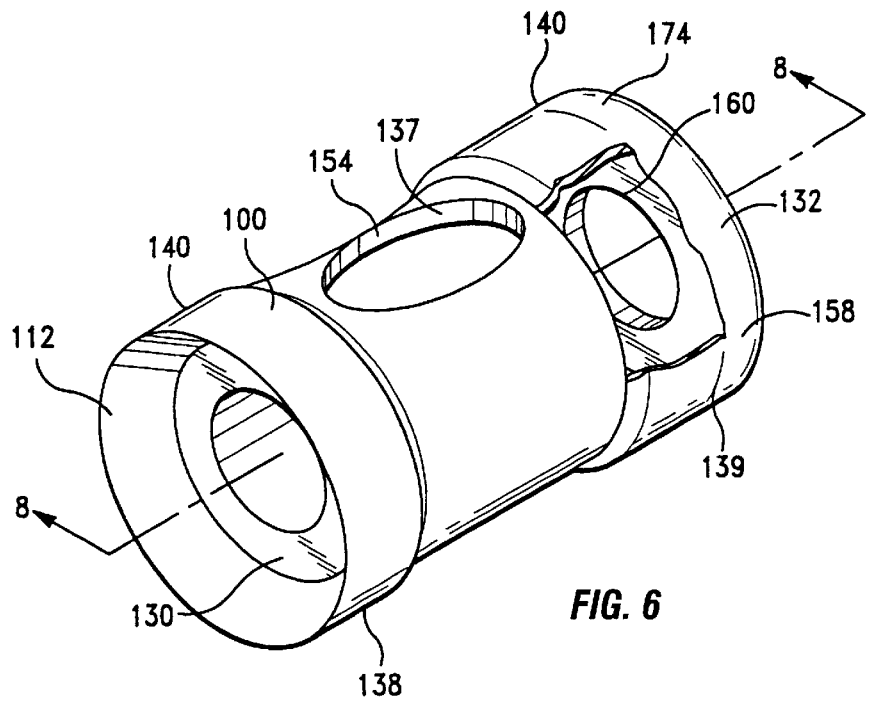
FIG. 6 is a perspective view of an embodiment of the composite cutter of FIG. 2.

With particular reference to FIG. 6, an embodiment of the composite cutter 100 is shown. A portion of the proximal end 139 of the cutter 140 and the sensor mount 130 are cut away to show an opening 160 which is defined by the proximal end 139. The opening 160 is adaptable for receiving, and bonding to, the cutter torque cable 126 (see FIG. 2).

The cutter 140 is machined to form an opening 154 having a periphery 137. The opening 154 permits communication between the sensor 164 (see FIG. 9 and FIG. 10) and the environment surrounding the cutter 140. When the sensor 164 attaches with the sensor mount 130, the sensor mount 130 and the cutter 140 cooperate to protect the sensor 164 from damage, hold the sensor 164, and align the sensor 164 relative to the cutting edge 112 of the cutter 140.

Figure 7:
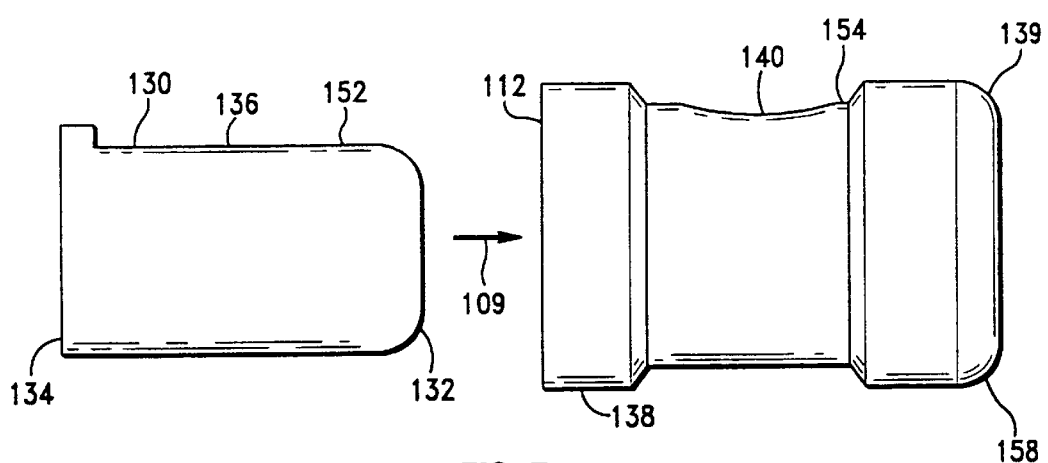
FIG. 7 is an exploded view of the composite cutter of FIG. 6.

With particular reference to FIG. 7, there is shown an exploded view of the composite cutter 100 of FIG. 6. An arrow 109 indicates that the sensor mount 130 inserts into the cutter 140 via the distal end 138 where the cutting edge 112 is situated.

The proximal end 139 of the cutter 140 has a rounded edge 158. The rounded edge 158 permits the cutter 140 to slide against biological tissue which may enter the cutter housing 104 during use of the atherectomy catheter 102 (see FIG. 1).

Figure 8:
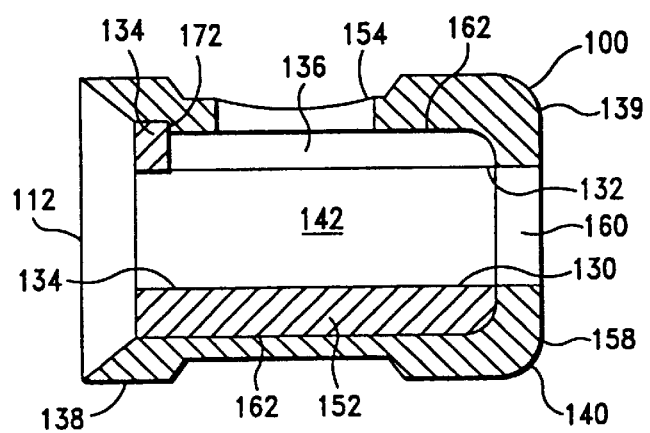
FIG. 8 is a cross-sectional view of an embodiment of the composite cutter of FIG. 6 as seen along the line 8—8.

With particular reference to FIG. 8, there is shown a cross-section of the composite cutter 100 of FIG. 6. The cutter 140 includes a proximal end 139, an interior surface 162, a distal end 138 and a ridge 172. The sensor mount 130 includes a proximal end 132, a distal end 134, and an interior 142. The sensor mount 130 attaches coaxially within the cutter 130. The interior 142 of the sensor mount 130 is cylindrical shaped, being configured for circumscribing the cutter torque cable 126 and being adaptable for attachment to the cutter torque cable 126.

The ridge 172 is formed on the interior surface 162 of the cutter 140 near the distal end 138 of the cutter 140. The ridge 172 contacts the distal end 134 of the sensor mount 130. The proximal end 139 of the cutter 140 contacts the proximal end 132 of the sensor mount 130. The ridge 172 and the proximal end 139 of the cutter 140 cooperate with the distal end 134 and the proximal end 132 of the sensor mount 130 respectively to hold the cutter 140 and the sensor mount 130 together. The outer surface 152 of the sensor mount 130 bonds to the interior surface 162 of the cutter 140.

Figure 9:
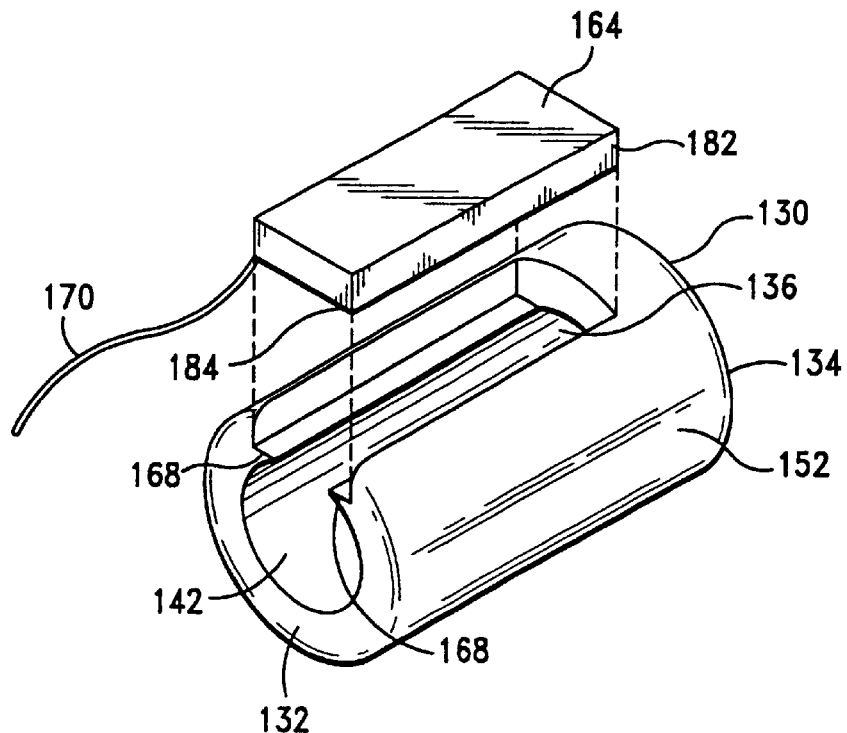
FIG. 9 is an exploded perspective view of an embodiment of the sensor mount of the composite cutter of FIG. 6.
Figure 10:
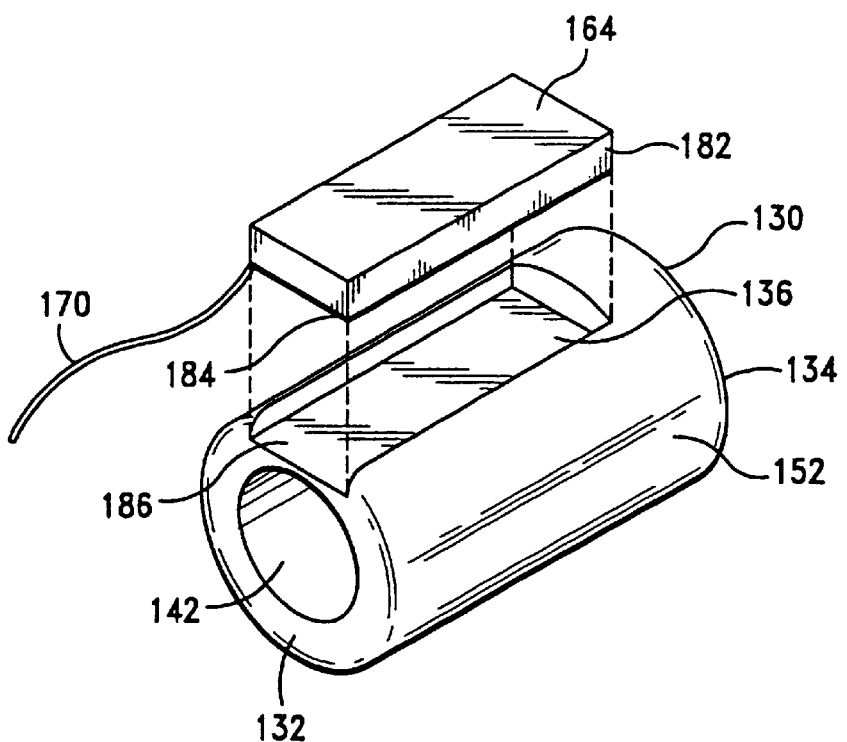
FIG. 10 is an exploded perspective view of another embodiment of the sensor mount of the composite cutter of FIG. 6.

With reference to both FIG. 9 and FIG. 10, variations of the sensor mount 130 are shown having a sensor 164. Each sensor mount 130 has a support 136. Each support 136 is machined into the exterior surface of the sensor mount 130. The sensor 164 is attachable with each support 136 by an adhesive bond. The support 136 is appropriately configured, having a rectangular shape, to coincide with the shape of sensor 164. The sensor 164 and the sensor mount 130 are sealed in a cover (not shown) such as a plastic wrap to protect the sensor 164 during use.

The sensor 164 communicates with an operator electronically via a wire 170 (partially shown) included with the sensor 164. The wire 170 extends from the sensor 164, through the opening 160 (see FIG. 6) and along the atherectomy catheter 102 (see FIG. 1) to appropriate signal processing equipment.

With particular reference to FIG. 9, an embodiment of sensor mount 130 is shown where the support 136 is a trough which cuts through the surface 152 into the interior 142 of the sensor mount 130. The sensor includes a periphery 184 and sides 182. Edges 168 of the support 136 hold the sensor 164 and bond to the sensor 164 at appropriate regions such as the side 182 and periphery 184 of the sensor 164. The proximal end 132 of the sensor housing 130 is rounded to conform in shape to the inner surface 162 of the cutter 140 (see FIG. 8).

With particular reference to FIG. 10, there is shown a variation of an embodiment of sensor mount 130 of FIG. 9 where the support 136 is a trough formed on the surface 152 of sensor mount 130. The support 136 includes a flat portion 186. The sensor 164 bonds with the flat portion 186 of the support 136.

Figure 11:
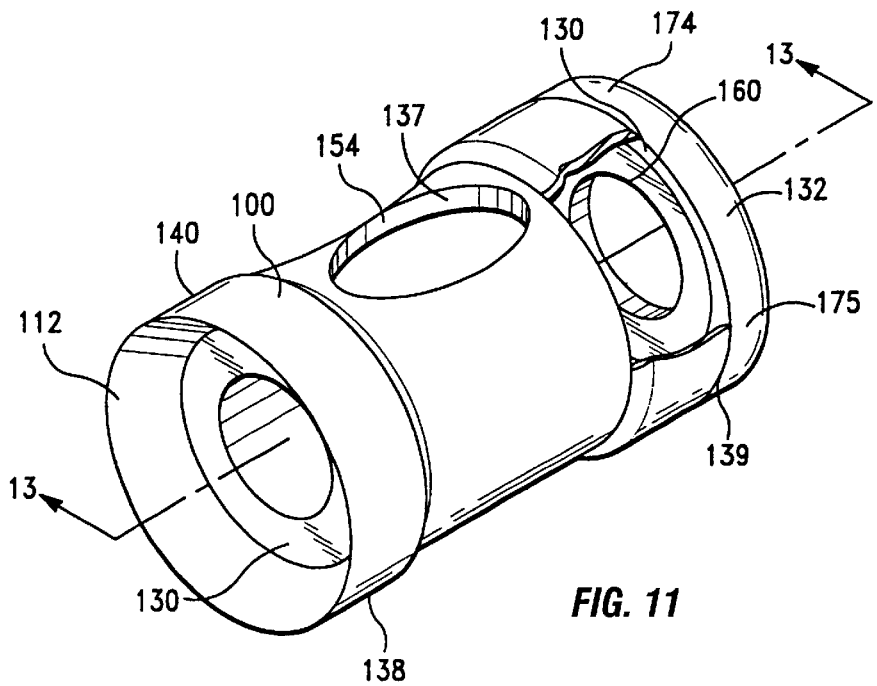
FIG. 11 is a perspective view of an embodiment of the composite cutter of FIG. 2.

With particular reference to FIG. 11 an embodiment of the composite cutter 100 of FIG. 2 is shown. The sensor mount 130 attaches within the cutter 140. A portion of the sensor mount 130 and the proximal end 139 of the cutter 140 are cut away to show the hole 160. The hole 160 is formed through the proximal end 139 of the cutter for circumscribing the cutter torque cable 126 when the cutter 140 bonds with the cutter torque cable 126. The cutter 140 defines a hole 154 having a periphery 137.

Figure 12:
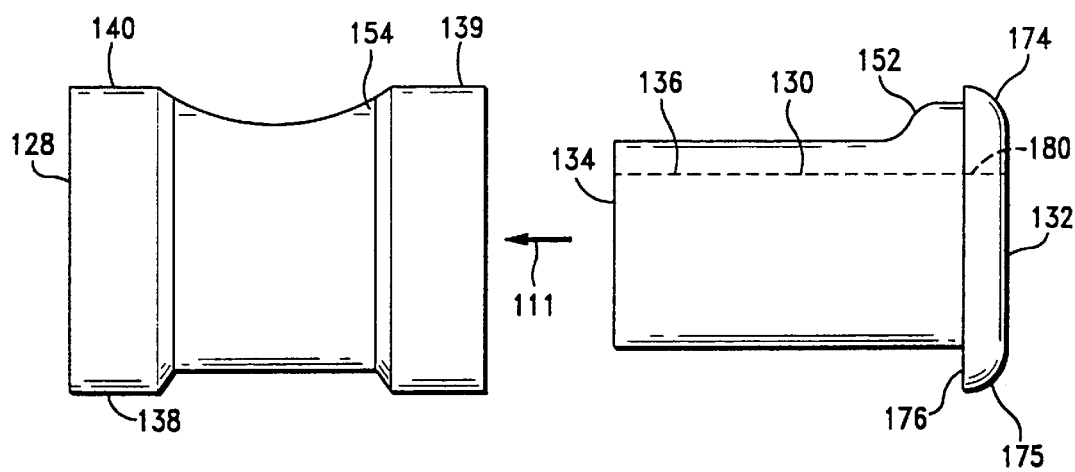
FIG. 12 is an exploded view of the composite cutter of FIG. 11.

With particular reference to FIG. 12, there is shown an exploded side view of the composite cutter 100 of FIG. 11. An arrow 111 indicates that the sensor mount 130 inserts into the cutter 140 via proximal end 139 of the cutter 140. A portion of the surface 152 of the sensor mount 130 is machined to form the support 136. The opening 154 is defined in the cutter 140. When the sensor mount 130 attaches to the interior surface 162 of the cutter 140, the opening 154 permits communication between the sensor 164 (shown in FIG. 14 and FIG. 15) and the environment which surrounds the composite cutter 100.

Figure 13:
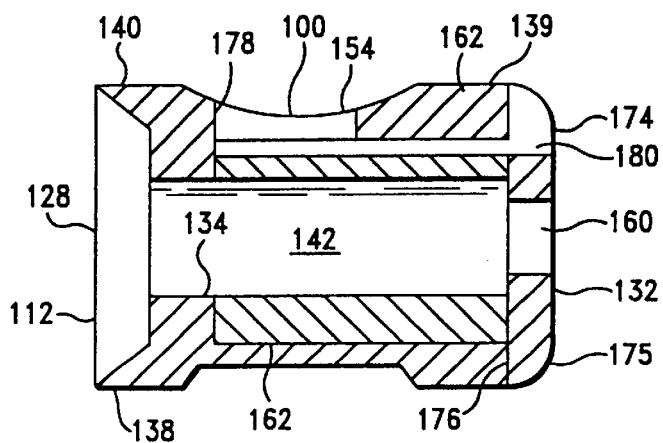
FIG. 13 is a cross-sectional view of an embodiment of the composite cutter of FIG. 11 as seen along the line 13—13.

With particular reference to FIG. 13, there is shown a cross-section of an embodiment of the composite cutter 100 of FIG. 11. The cutter 140 has a proximal end 139, an interior surface 162 having a seat 178, and a distal end 138. The sensor mount 130 includes a surface 152 and a cap 175 formed with a rounded edge 174 and an annular shoulder 176. The cap 175 is affixed at the proximal end 132 of the sensor mount 130. The surface 152 of the sensor mount bonds with the interior surface 162 of the cutter 140. The cap 175 of the sensor mount 130 contacts the proximal end 139 of the cutter 140. The distal end 138 of the sensor mount 130 contacts the seat 178. The seat 178 has an arcuate geometry which meets securely with the distal end 138. The interior surface 162, the proximal end 130, and the seat 178 of the cutter 140 cooperate to hold the sensor mount 130.

Figure 14:
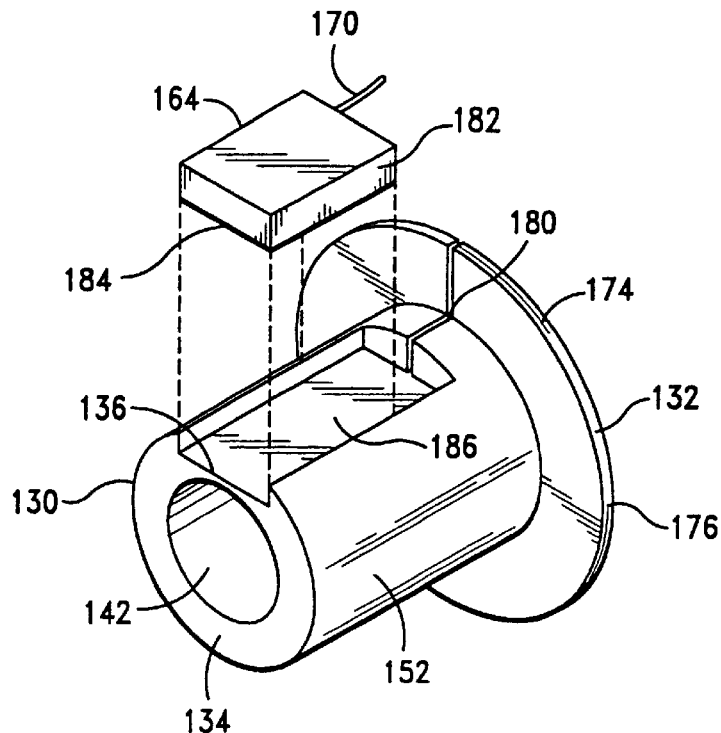
FIG. 14 is an exploded perspective view of an embodiment of the sensor mount of the composite cutter of FIG. 11.
Figure 15:
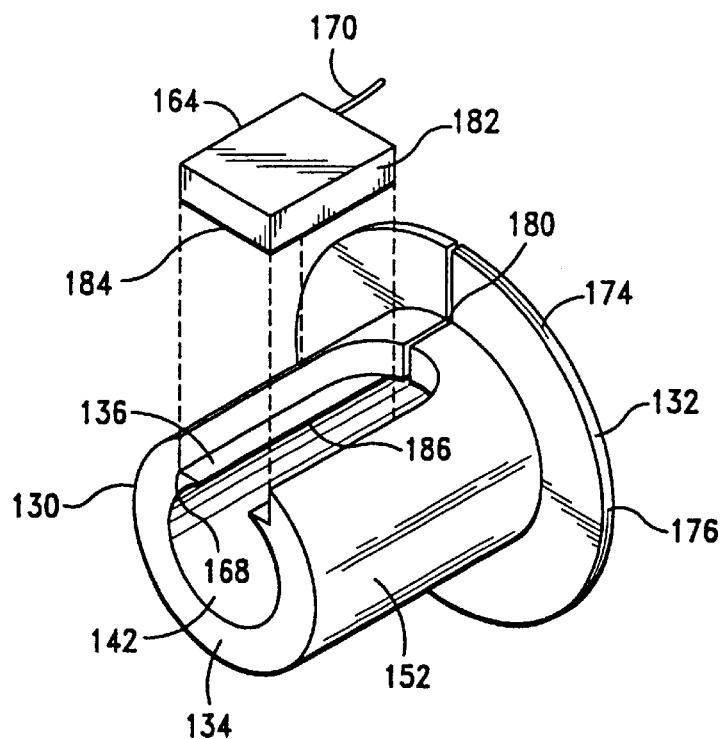
FIG. 15 is an exploded perspective view of another embodiment of the sensor mount of the composite cutter of FIG. 11.

With reference to both FIG. 14 and FIG. 15, sensor mount 130 is shown having a sensor 164 positioned adjacent the support 136. The support 136 is adaptable to conform with the shape of the sensor 164 (i.e. includes a geometry capable of holding the sensor 164). Both the support 136 and the sensor 164 are rectangular shaped and are adhesively bonded together. The sensor 164 communicates with an operator electronically via a wire 170 included with sensor 164. The wire 170 extends from sensor 164, along a conduit 180 formed through cap 175 and out through the atherectomy catheter 102 to electrically communicate with a sensor system (not shown).

With particular reference to FIG. 14, the sensor mount 130 of FIG. 13 is shown. The support 136 is a trough formed in the surface 152 of sensor mount 130. The sensor 164 bonds to the flat portion 186 of the support 136.

With particular reference to FIG. 15, a variation of the embodiment of sensor mount 130 of FIG. 14 is shown. The support 136 is a trough which cuts into the interior 142 of sensor mount 130. The edges 168 hold the sensor 164 in place and provide a bonding surface. More particularly, the edges 168 bond to appropriate regions of the sensor 164 such as the side 182 and periphery 184.

Figure 16:
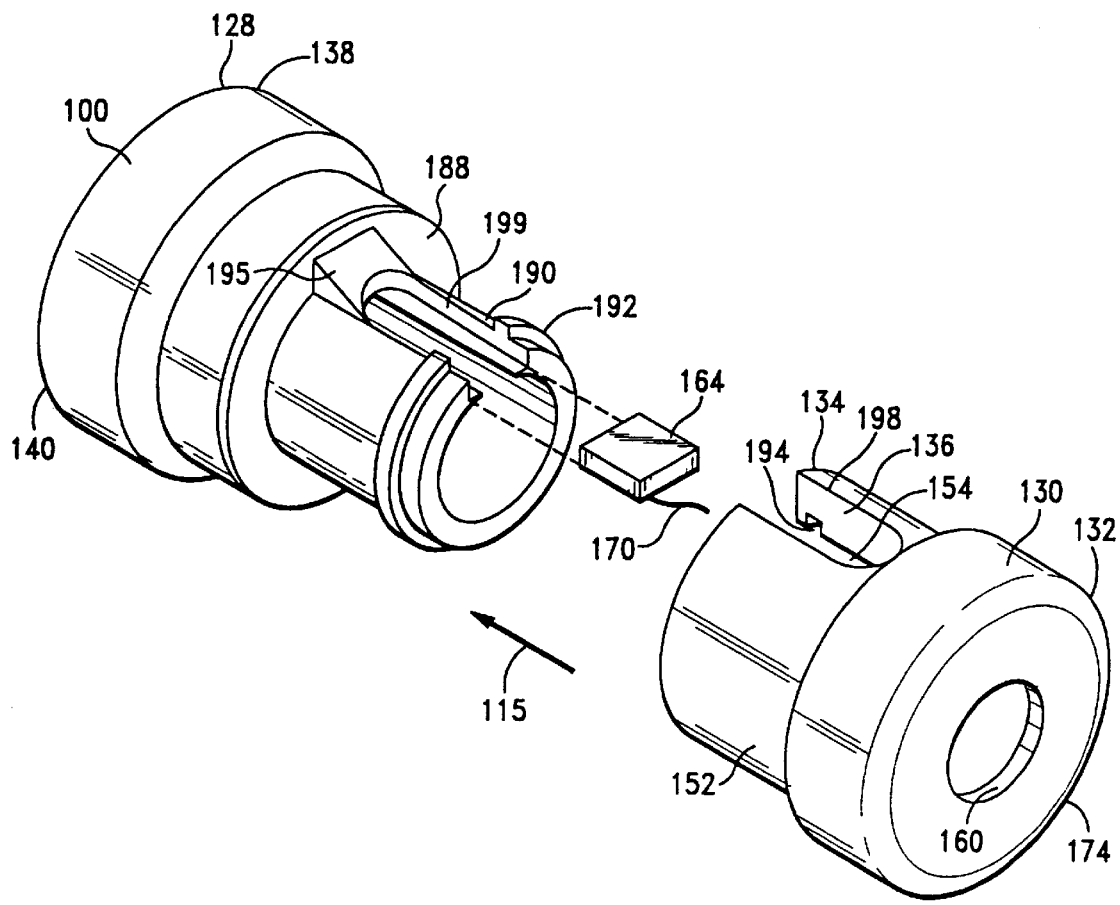
FIG. 16 is an exploded perspective view of an embodiment of the composite cutter of FIG. 2.

With particular reference to FIG. 16, an embodiment of the composite cutter 100 of FIG. 1 is shown. The cutter 140 includes an annular face 188, a cylindrical extension 190, an annular ring 192 and a guide 196. The cylindrical extension 190 extends perpendicularly from the annular face 188 of the cutter 140. The annular ring 192 circumscribes the cylindrical extension 190. The cylindrical extension 190 is adaptable to circumscribe and bond with the cutter torque cable 126.

The sensor mount 130 includes an internal annular groove 194. The annular ring 192 of the cylindrical extension 190 snaps into the internal annular groove 194 in the sensor mount 130 to mechanically interconnect the sensor mount 130 and the cutter 140.

The sensor mount 130 is fabricated from a plastic and attaches to the cutter torque cable 126 via heat bonding. In a preferred embodiment, the sensor mount is fabricated from a material selected from the following group: poly-carbonate and polypropylene.

The cylindrical extension 190 extends perpendicularly from annular face 188 of the cutter 140. The cylindrical extension 190 attaches with the sensor mount 130 and includes a hollow interior for receiving and bonding with the cutter torque cable 126.

The cylindrical extension 190 includes a guide 196. The guide 196 includes a triangular cross-section which extends between the annular face 188 and the cylindrical extension 190. The guide 196 contacts with the edge 198 of the opening 154 and aligns the sensor mount 130 into a desired position with the cutter 140. During operation, the guide 196 contacts the sensor mount 130 so that the sensor mount 130 and the cutter 140 rotate together. The guide 196 may include a reflective coating to reflect ultrasonic energy radiated by the sensor 164.

The sensor 164 is shown between the cutter 140 and the sensor mount 130. Communication between the sensor 164 and the environment surrounding the composite cutter is established via the opening 154. Electronic communication is established between the sensor 164 and a sensor system via the wire 170 (shown in part) which passes through the sensor mount 130, the opening 160 and through the atherectomy catheter 102 (see FIG. 1).

The cutter 140 has an edge 199 and the sensor mount 130 has an edge 198. When the cutter 140 and the sensor mount 130 attach, the edges 198 and the edge 199 conform to the shape of the sensor 164. The edge 198 and the edge 199 are configured to hold the sensor 164. The sensor 164 adhesively bonds to the edge 198 and to the edge 199. An arrow 115 indicates the direction in which the sensor mount 130 mates with the cutter 140.

Numerous methods of bonding the sensor mount 130 to the cutter 140 exist. In one variation of an embodiment of the present invention, the sensor mount 130 attaches to the cutter 140 via injection molding. In another variation, the sensor mount 130 bonds to the support 136 adhesively.

Numerous methods of bonding the composite cutter 100 to the cutter torque cable 126 exist. Each method of bonding depends on the geometry and the material to be bonded. For example, a bonding method may first be chosen for the cutter 140 and the sensor mount 130 which is based on the material composition of the parts to be joined. The sensor mount 130 and the cutter 140 are then configured having an appropriate geometry, suitable for the chosen bonding method in accordance with industry standards and practical cost constraints. With any geometry, however, precise alignment between the sensor mount 130 and the cutter 140 is desirable.

The sensor mount 130 is fabricated from a machinable or conformable material which is adaptable to provide an appropriate support 136 for a sensor, or a sensor system for example. The cutter 140 is fabricated from a material of an appropriate hardness to resist deformation such as dulling. Materials such as diamond, cubic boron nitride and other materials could be used to form portions of the cutter such as the cutting edge 112. An appropriate coating can be applied to the composite cutter 100, or portions thereof, for increased bio-compatibility or wear resistance, for example. In a preferred embodiment, the cutter 140 has a coating of titanium nitride.

Figure 17:
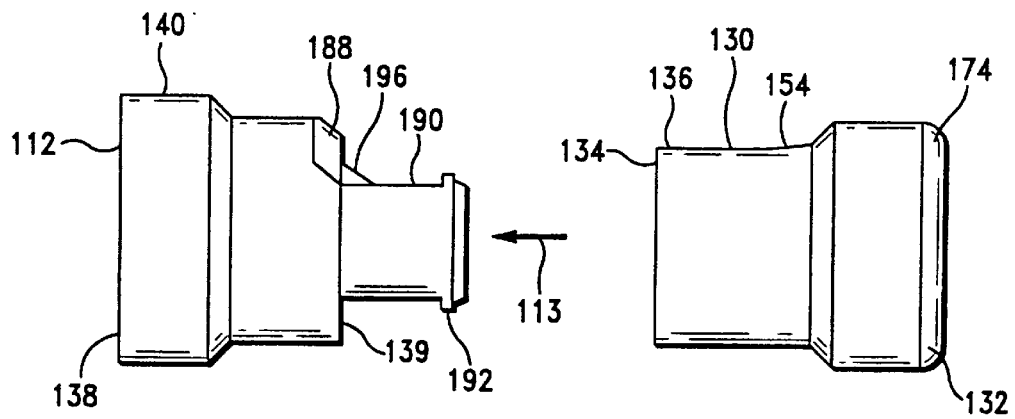
FIG. 17 is an exploded side view of the composite cutter of FIG. 16.

With particular reference to FIG. 17, an exploded view of the composite cutter 100 of FIG. 16 is shown. An arrow 113 indicates the direction in which the sensor mount 130 connects with the cutter 140 via proximal end 139. A portion of the surface 152 of the sensor mount 130 is machined to form the support 136 which includes the opening 154.

Examples of the sensor 164 and the atherectomy catheter 102 are described in U.S. Pat. No. 5,429,136, Issue date Jul. 4, 1995, entitled "Imaging Atherectomy Apparatus" by Milo et al. which is assigned to the assignee of the present invention and which is incorporated herein by reference.

Although the sensor 164 is shown having a rectangular shape, a variety of shapes can be accommodated by the present inventive concept. For example, the support 136 can be adapted to coincide with the shape of a square, or circular shaped sensor. The support can be formed within the cutter 140, on the sensor mount 130, or any other suitable alternative which holds the sensor 164 and permits communication between the sensor 164 and the environment.

A sensor capable of generating and communicating a description of the interior of a blood vessel is employed by the present invention. The sensor 164 is an ultrasonic transducer which is capable of determining the density of surrounding tissues during operation of the present invention. The sensor 164 communicates with an operator by the wire 170 which may be wrapped about the surface 152 of the sensor mount and securely held by, for example, a plastic wrap, or an adhesive. The wire 170 extends through the atherectomy catheter 102 to establish electronic communication with an operator.

The foregoing detailed description has described the composite cutter 100 in terms of various embodiments. It is to be understood that the above description is illustrative only, and does not the scope of disclosed invention. Particularly, the specific details of the cutting edge can differ from those illustrated and described so long as the cutting is enabled. It will be appreciated that the shape and situs of the support 136 which holds the sensor 164 can differ from that disclosed so long as the sensor communicates with the environment surrounding the composite cutter 100. The shape of the composite cutter 100 can vary. Although specific details of the present invention are disclosed as above, the scope of the present inventive concept is to be limited only by the claims set forth below.

We claim:

1. An atherectomy device for cutting material from the inside of a biological conduit, comprising:

a catheter having a housing and a rotatable cutter torque cable, the catheter being insertable into the biological conduit, the cutter torque cable extending through the catheter to the housing;

a sensor mount having a proximal end and a distal end, the proximal end of the sensor mount being attached to the cutter torque cable and being adaptable for holding a sensor, the sensor mount rotates with the cutter torque cable; and a cutter having a proximal end, a distal end and a cutting edge, the cutting edge being formed on the distal end of the cutter, the cutter being attached with the sensor mount to rotate with the cutter torque cable, whereby when the catheter is inserted into a biological conduit, the cutter and the sensor mount move within the housing in response to movement of the cutter torque cable to cut material from inside of the biological conduit.

2. A device as set forth in claim 1, wherein the proximal end of the sensor mount defines an interior which is attachable to the cutter torque cable, the proximal end of the sensor mount includes an attachment hole which enables the sensor mount to be attachable with the cutter torque cable.

3. A device as set forth in claim 1, wherein the sensor mount is fabricated from machinable grade stainless steel and the cutter is fabricated from tungsten carbide.

4. A device as set forth in claim 1, wherein the cutter includes a coating to increase the hardness of the cutting edge.

5. A device in as set forth in claim 4, wherein the coating is fabricated from titanium nitride.

6. A device as set forth in claim 1, wherein the sensor mount includes a trough, the trough being configured having a geometry adaptable for holding a sensor.

7. A device as set forth in claim 6, wherein the sensor mount includes a periphery, the periphery is adaptable for bonding to a sensor.

8. An atherectomy device for cutting hard material from the inside of a blood vessel comprising:

a catheter having a housing and a rotatable cutter torque cable, the catheter being insertable into the blood vessel, the cutter torque cable extending through the catheter to the housing;

a sensor mount having a proximal end and a distal end, the proximal end of the sensor mount being attachable to the cutter torque cable;

a sensor attached to the sensor mount; and a cutter having a proximal end, a distal end and a cutting edge, the cutting edge being formed on the distal end, the proximal end of the cutter being attached with the sensor mount, whereby the cutter torque cable rotates the cutter, the sensor and the sensor mount move within the housing in response to movement of the cutter torque cable to cut material from the inside of a blood vessel.

9. An atherectomy device capable of holding an imaging sensor comprises:

an atherectomy catheter formed with a cutter housing, a window, a nosecone attached to the cutter housing, and a cutter torque cable aligned centrally along the atherectomy catheter, the cutter torque cable being rotatable;

a sensor mount positioned within the housing, the sensor mount being formed of a material having a machinable hardness, the sensor mount being attached to the cutter torque cable for rotating with the cutter torque cable;

an ultrasonic transducer attached with the sensor mount, the transducer being rotatable with the sensor mount and being capable of imaging; and a cutter attached to the sensor mount, the cutter being formed having a cutting edge with a hardness relatively greater than the machinable hardness of the sensor mount, whereby the sensor mount circumscribes the cutter torque cable, the cutter and the sensor mount form a composite structure which is rotatable with the cutter torque cable.

* * * * *